United States Patent [19]

Utne et al.

[11] 4,329,469

[45] May 11, 1982

[54] DISPLACEMENT PURIFICATION OF SALTS

[75] Inventors: Torleif Utne, Warren; Ronald B. Jobson, East Brunswick, both of N.J.

[73] Assignee: Merck & Co., Inc., Rahway, N.J.

[21] Appl. No.: 209,814

[22] Filed: Nov. 24, 1980

[51] Int. Cl.³ .............................................. C07D 211/70
[52] U.S. Cl. ..................................... 546/203; 546/204
[58] Field of Search ................................ 546/203, 204

[56] References Cited

PUBLICATIONS

Paul Pfeiffer, Organische Molekulverbindungen (1927), p. 129.
Houben-Weyl, Methoden der Organischen Chemie, vol. I/1 (1958), pp. 457–461.
A. Blanchard et al., Synthetic Inorganic Chemistry (1930), pp. 114–115.
Collet et al., Chem. Rev. 80, 215 (1980).
Wong et al., Tetrahedron Letters 40, 3813 (1978).
Wilen et al., Tetrahedron, 33, 2725 (1977).
Horeau, Tetrahedron, 31, 1307 (1975).

*Primary Examiner*—Norma S. Milestone
*Attorney, Agent, or Firm*—William H. Nicholson; Mario A. Monaco

[57] ABSTRACT

An optically impure diastereomeric salt is purified by treating a suspension of the salt in an appropriate solvent or solvent mixture with the required amount of the desired, optically pure, acid or base.

3 Claims, No Drawings

DISPLACEMENT PURIFICATION OF SALTS

SUMMARY OF THE INVENTION

This invention is concerned with a process for the purification of a salt of an acidic or basic organic compound which is contaminated with a similar salt of an isomer, homolog or analog of the same organic compound, wherein the contaminating salt is the more soluble. The process comprises treating the impure salt with an amount of the pure organic compound which is chemically equivalent to the amount of the contaminating isomer, homolog, or analog. The process results in the displacement of the impurity by the desired organic compound in the salt structure thereby resulting in a purified salt.

The process is of particular value in purifying one of the diastereomeric salts encountered in a typical optical resolution. It is also useful in separating geometric isomers such as cis-trans, position isomers, and simple analogs and homologs where their salts or complexes have similar properties.

BACKGROUND OF THE INVENTION

Usually, after formation of diastereomeric salts in a resolution procedure, one of the pair will preferentially crystallize in a somewhat optically impure form. Purification of this salt frequently requires repeated recrystallizations involving large volumes of solvents and loss of time and of yield.

Now with the present invention a single operation, stirring the impure salt with the desired isomer, provides the desired salt in about 90% yield and 99% optical purity. The same principle is applicable to the separation of other types of isomers and simple homologs and analogs.

DETAILED DESCRIPTION OF THE INVENTION

The novel process of this invention comprises treating an impure salt of formula

A.(B,B')

suspended in a liquid medium in which the salt is substantially insoluble, and wherein
- B is a basic or acidic organic compound soluble in the liquid medium;
- B' is an isomer, homolog or analog of B, also soluble in the liquid medium and comprising 10–30% of combined (B,B') on a molar basis;
- A is an acidic or basic organic compound capable of forming a salt with B and B' with an amount of pure B equivalent to that represented by B', whereby B' is displaced from the salt A.(B,B') to produce the salt A.B of about 99% optical purity.

In the novel process of this invention the liquid medium is normally an inert, aprotic organic solvent, in which the salt, A.B is substantially insoluble and the organic compounds B and B' are soluble, such as toluene, benzene, or the like.

The volume of solvent is not critical but should be chosen so that the above-described solubility requirements are met and so that there are about 5 to 30 ml. of solvent per gram of salt, preferably about 10 to about 20 ml. per gram.

The process is conducted by agitating the mixture of starting materials by stirring or shaking until the exchange of B for B' is substantially complete. The time required will vary from about 2 to about 48 hours, usually about 10 to about 24 hours. It is convenient to run the process overnight, that is, for about 16 hours.

The temperature at which the process is conducted can vary widely from about −80° C. to the boiling point of the solvent. A preferred range is about 20° C. to about 60° C. and most conveniently about room temperature.

In a preferred embodiment of the novel process of this invention, the impure salt represented as A.(B,B') is one member of the diastereomeric pair of salts encountered in an optical resolution in which case B represents one optical isomer contaminated with some of its optical antipode B' and A represents one optical isomer of an optically active compound capable of forming a salt with B and B'.

In a still more preferred embodiment B and B' are organic bases such as an amine, preferably a tertiary amine and A represents an optically active carboxylic acid.

In a most preferred embodiment, the compound B has structural formula:

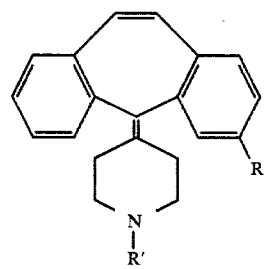

(−)-isomer wherein R is
(1) —CN,
(2) —SCF$_3$,
(3) —SO$_2$CF$_3$,
(4) —OCH$_3$ or
(5) halo, such as chloro, bromo, iodo or fluoro
and R' is
(1) —CH$_3$ or
(2) —CH$_2$
Also, in the most preferred embodiment, A is di-p-toluoyl-d-tartaric acid.

EXAMPLE 1

Purification of optically impure diastereomeric salt

Step A: Preparation of diastereomeric salt

To a solution of 387 g (0.906 mole) of (±)-1-cyclopropylmethyl-4-(3-trifluoromethylthio-5H-dibenzo[a,d]cyclohepten-5-ylidene)piperidine (I) in 3870 ml of toluene containing 19 ml of methanol at room temperature (22°) was added 220 g (0.569 mole) of di-p-toluoyl-d-tartaric acid. A complete solution resulted within three minutes followed by rapid crystallization of the desired tartrate salt. The mixture was stirred vigorously at room temperature (23°) overnight. The crystalline product was collected by filtration, washed with 1 l. of toluene and dried under vacuum at room temperature to yield 355 g (86.5% physical yield) of (−)-1-cyclopropylmethyl-4-(3-trifluoromethylthio-5H-dibenzo[a,d]-cyclohepten-5-ylidene)piperidine di-p-toluoyld-tartrate, as the toluene solvate (II), m.p. 142°–146° dec., $[\alpha]_D^{25} -91.3°$ (C=1, EtOH). A sample of this salt was converted to the free base and had a m.p. of 142°–145° dec., $[\alpha]_D^{25} -58.0°$ (C=1, CH$_2$Cl$_2$) indicating 87% optical purity (O.P.).

Step B: Purification of diastereomeric salt

To a stirred slurry of 10 g of optically very impure (71% o.p.) di-p-toluoyl-d-tartrate (DTTA) salt of (−)-1-cyclopropylmethyl-4-(3-trifluoromethylthio-5H-dibenzo[a,d]cyclohepten-5-ylidene)-piperidine, as the toluene solvate, (II), in 200 ml of toluene was added 750 mg of pure free base of compound (II). The mixture was stirred overnight at 50°–60° C., the purified salt was filtered off, washed with 50 ml of toluene and 50 ml of hexane and dried under vacuum overnight at 24° to yield 9.6 of 92% optically pure tartrate salt (yield 92% of theory, inclusive base added); mp. 144°–147° (d); $[\alpha]_D^{25} -94.0°$ (1%, EtOH)~97% o.p. on salt; $[\alpha]_D^{25} -60.7°$ (1%, CH$_2$Cl$_2$)~92% o.p. on free base.

EXAMPLE 2

Purification of diastereomeric salt

To a stirred slurry of 10 g of II tartrate salt (87% o.p.) in 100 ml of toluene containing 2% methanol was added 325 mg of pure free base II and stirred at 22° overnight. The purified salt was filtered off, washed with 50 ml of toluene and 50 ml of hexane, dried under vacuum overnight at 22° to yield 9.2 g of 99% optical purity (yield 91% of theory, inclusive base added), m.p. 146°–148° (d); $[\alpha]_D^{25} -97.8°$ (1%, EtOH)~100% o.p. on salt; $[\alpha]_D^{25} -65.4°$ (1%, CH$_2$Cl$_2$)~99% o.p. on free base, mp. 143°–146° (d).

EXAMPLE 3

Purification of diastereomeric salt

To a stirred slurry of 428 g of the DTTA salt (II) (89% o.p.) in 4.28 l. of toluene containing 2% methanol was added 12 g of pure free (−)-base and stirred at room temperature (22°) overnight. The purified salt was collected, washed with 1 l. of toluene and dried in vacuo overnight at room temperature to yield 380 g (89%), mp 146°–148° (d), of pure DTTA toluene solvate salt (II). A sample converted to the free base in the usual manner had a mp. of 143°–146° (d), $[\alpha]_D^{25} -66°$ (1%, CH$_2$Cl$_2$) indicating 99% o.p.

Titration with NaOH: 100.6% of theory.

Anal. calcd. for $C_{25}H_{24}F_3NS \cdot C_{20}H_{18}O_8 \cdot C_7H_8$: C, 68.90; H, 5.56; N, 1.55; S, 3.53: Found C, 68.58; H, 5.52; N, 1.49; S, 3.57.

Employing the procedure of Example 1 Step A followed by that of Examples 1 Step B, Example 2, or Example 3, but substituting for (±)-1-cyclopropylmethyl-4-(3-trifluoromethylthio-5H-dibenzo[a,d]cyclohepten-5-ylidene)piperidine, used in Example 1, Step A, each of the racemic compounds identified in Table I, there are produced the purified diastereomeric salts also described in Table I:

TABLE I

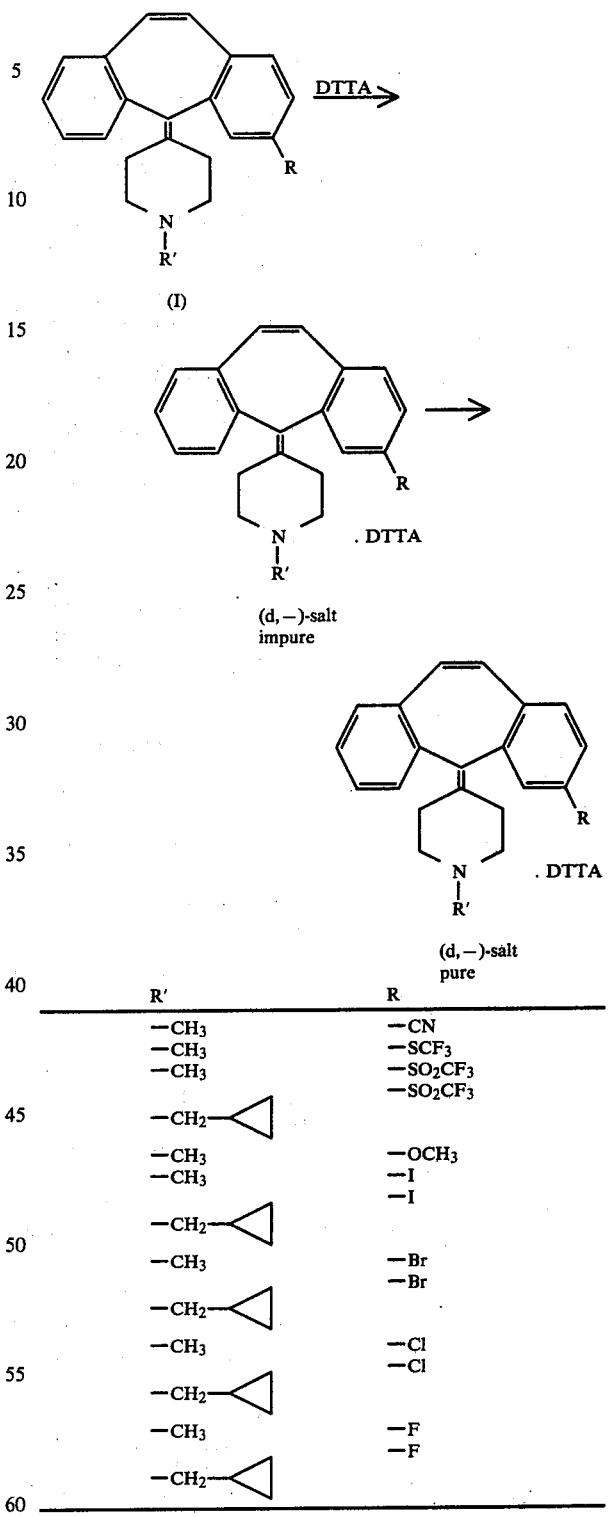

| R' | R |
|---|---|
| —CH$_3$ | —CN |
| —CH$_3$ | —SCF$_3$ |
| —CH$_3$ | —SO$_2$CF$_3$ |
| —CH$_2$—◁ | —SO$_2$CF$_3$ |
| —CH$_3$ | —OCH$_3$ |
| —CH$_3$ | —I |
| —CH$_2$—◁ | —I |
| —CH$_3$ | —Br |
| —CH$_2$—◁ | —Br |
| —CH$_3$ | —Cl |
| —CH$_2$—◁ | —Cl |
| —CH$_3$ | —F |
| —CH$_2$—◁ | —F |

What is claimed:

1. A process for the purification of a diastereomeric salt of formula:

A.(B,B')

wherein

B is a basic optically pure organic compound;

B' is an optical antipode of B comprising 10–30% of combined (BB') on a molar basis;

A is one enantiomer of an acidic optically active organic compound capable of forming a salt with B and B'; which comprises the steps of:

(1) suspending the impure salt, A.(B,B'), in an aprotic organic liquid in which the salt is substantially insoluble and in which A, B and B' are appreciably soluble;

(2) adding an amount of pure B equimolecular with the amount of B' in the impure salt; and (3) agitating the mixture;

whereby B' in the impure salt is replaced by B to form the more pure salt A.B.

2. The process of claim 1 wherein B is:

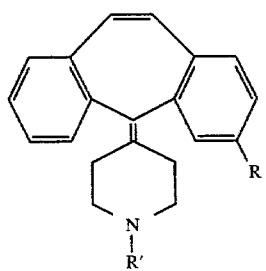

(−)-isomer wherein R is
(1) —CN,
(2) —SCF$_3$
(3) —SO$_2$CF$_3$
(4) —OCH$_3$ or
(5) —halo; and R' is
(1) —CH$_3$ or
(2)

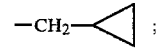

and
A is di-p-toluoyl-d-tartaric acid.

3. The process of claim 2 wherein
R is —SCF$_3$; and
R' is

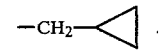

* * * * *